United States Patent [19]
Carney et al.

[11] Patent Number: 6,080,844
[45] Date of Patent: Jun. 27, 2000

[54] PROCESS FOR THE RECOVERY AND PURIFICATION OF A RECOMBINANT PROTEIN FROM A CELL

[75] Inventors: Ronald E. Carney, Winthrop Harbor, Ill.; Joseph Arndt, Columbus, Ohio; Julie R. List; Ellen Marie Schwartz, both of Waukegan, Ill.

[73] Assignee: Abbott Laboratories, Abbott Park, Ill.

[21] Appl. No.: 09/065,224

[22] Filed: Apr. 23, 1998

[51] Int. Cl.$^7$ ...................................................... C07K 1/14
[52] U.S. Cl. ........................ 530/361; 530/360; 530/350; 530/412; 530/418; 530/419; 530/420; 530/424; 530/422; 435/69.1; 435/252.3; 435/320.1
[58] Field of Search ..................................... 530/361, 350, 530/412, 418, 419, 420, 422, 424, 360; 435/9.1, 252.3, 320.1

[56] References Cited

U.S. PATENT DOCUMENTS

| | | | |
|---|---|---|---|
| 5,710,044 | 1/1998 | Mukerji et al. | 435/320.1 |
| 5,739,407 | 4/1998 | Bergstrom et al. | 800/2 |

FOREIGN PATENT DOCUMENTS

| | | |
|---|---|---|
| 9110677 | 7/1991 | WIPO . |
| 9406306 | 3/1994 | WIPO . |

OTHER PUBLICATIONS

Hipp et al. (1952) J. Dairy Sci. 35:272–81.
Hansson et al. (1993) Protein Expression and Purification 4:373–81.
Mulvihill (1989) Developments in Dairy Chem. 4:97–130.
Derwent Publications Ltd., London, GB; AN 91–102657, XP002110124 & DD 284 110 A (Humboldt–Univ. Berlin), Nov. 7, 1990 abstract.
Scopes, R.K.: "Protein Purification—Principles and Practice. Ch.2 ('Making an extract') & 3 (Separation by precipitation)." 1987, Springer–Verlag, New York XP002109597 p. 26–33; p. 45–62.
Dyr, J.E. et al.: "Separation use for purification of recombinant proteins", Journal of Chromatography B: Biomedical Sciences & Applications, vol. 699, No. 1–2, Oct. 10, 1997, p. 383–401, XP004095005, ISSN: 0378–4347 p. 8, p. 11–col. 2, p. 13–col. 1, p. 14–col. 2, p. 16–col. 1.
Novella, et al.: "Improvement of the extraction of penicillin acylase from *Escherichia coli* cells by a combined use of chemical methods", Biotechnology and Bioengineering, vol. 44, 1994, pp. 379–382, XP002109997, abstract, p. 2, left–hand col., line 4–7.
Hipp, et al.: "Separation of alpha–, beta– and gamma–casein.", J. Dairy Sci., vol. 35, 1952, XP002109595 (whole document) pp. 272–281.
Mulvihill, D.M.: "Caseins and caseinates: Manufacture" IN: Developments in Dairy Chem., vol. 4, Fox, ed. pp. 97–130, Elsevier Appl. Sci. Publ. London, 1989, XP002109621, p. 97–103, p. 112, paragraph 3, p. 115–119, p. 123–124.
F. M. Ausubel et al., eds., *Current Protocols in Molecular Biology*, vol. 2, John Wiley & Sons, Inc., (1993), pp. 10.9.2.

*Primary Examiner*—Enrique D. Longton
*Attorney, Agent, or Firm*—Lawrense S. Pope; Gregory W. Steele

[57] ABSTRACT

The present invention involves a process of purifying and recovering a recombinant protein from a suspension of cells. The process of the present invention involves extracting a recombinant protein from a concentrated suspension of cells using a water-miscible organic solvent, isolating the recombinant protein from the suspension of cells, concentrating the recombinant protein to remove the water-miscible organic solvent, precipitating the recombinant protein using an acid, washing the recombinant protein with the salt or free form of a suitable organic acid and recovering the recombinant protein.

5 Claims, No Drawings

PROCESS FOR THE RECOVERY AND PURIFICATION OF A RECOMBINANT PROTEIN FROM A CELL

TECHNICAL FIELD OF THE INVENTION

The present invention relates to a process of purifying and recovering a recombinant protein from a cell.

BACKGROUND OF THE INVENTION

Typically, proteins are purified using conventional chromatography or high-performance liquid chromatography methods. Chromatographic methods that can be used to purify proteins include gel-filtration chromatography, ion-exchange chromatography, immunoaffinity chromatography and metal-chelate affinity chromatography. The high-performance liquid chromatographic methods that can be used to purify proteins include reverse-phase high-performance liquid chromatography, ion-exchange high-performance liquid chromatography, size-exclusion high-performance liquid chromatography and high-performance chromatofocusing and hydrophobic interaction chromatography.

Purification of proteins by conventional chromatography is usually achieved using a combination of chromatographic methods including gel-filtration, ion-exchange, hydrophobic-interaction, dye-interaction, affinity and immunoaffinity chromatography. With the possible exception of affinity or immunoaffinity chromatography, it is rarely possible to purify a protein to homogeneity in a single chromatographic step (see Current Protocols in Molecular Biology, Vol. 2, 10.9.2, Ausubel et al., eds. 1993). If affinity or immunoaffinity columns are not available for purifying a particular protein, then it is typically necessary to utilize sequential chromatographic steps and to analyze (such as by one-dimensional gel electrophoresis) the protein after each purification step, to determine if the protein is homogeneous. Id.

Purification of proteins by high-performance liquid chromatography (HPLC) relies on the use of rigid, small-particle matrices at high operation pressure. Id. at 10.12.1. Unlike conventional chromatography, HPLC is most suitable for purifying low-microgram quantities of proteins collected in small fraction volumes with a short separation time. Id. The limitation of small sample load results from the low-loading capacity of commercially available, analytical HPLC columns. Id. Typically, HPLC is used most frequently in later stages of protein purification, typically after one or more conventional chromatographic separations have been used to reduce the mass of contaminating proteins and to simplify a complex protein mixture. Id.

As discussed earlier, one of the problems with conventional chromatography or high-performance liquid chromatography methods is that it is rarely possible to purify a protein to homogeneity in a single step using either of these methods. Additionally, conventional chromatography or high performance liquid chromatography methods are labor intensive and these methods are expensive to use.

Thereupon, there is a need in the art for a process that can be used to purify proteins to homogeneity in a single step, is inexpensive to use and is not labor intensive.

SUMMARY OF THE INVENTION

The present invention relates to a process of purifying and recovering a recombinant protein from a cell. The process of the present invention involves extracting a recombinant protein from a concentrated suspension of cells with a water-miscible organic solvent. The water-miscible solvent contains from about 50% volume to about 95% volume of an organic solvent and from about 50% volume to about 5% volume of water. The recombinant protein is treated with a water-miscible organic solvent at a pH of from about 5.0 to about 10.0 and at a temperature of from about 30° C. to about 50° C. Examples of organic solvents are acetone, isopropanol, ethanol and methanol.

After extraction of the recombinant protein from the suspension of cells, the recombinant protein is isolated from the suspension of cells. After isolation, the recombinant protein is concentrated to remove the water-miscible organic solvent. After concentration, the recombinant protein is precipitated using an acid. The recombinant protein is precipitated using the acid at a pH of from about 3.5 to about 6.5. After precipitation, the recombinant protein is washed with a washing solution. Exemplary washing solutions are sodium acetate, citric acid, acetic acid, sodium citrate and the like. Finally, after washing, the recombinant protein is recovered.

In a preferred embodiment, the present invention also relates to a process for purifying and recovering recombinant beta-casein from a cell. The process of purifying and recovering recombinant beta-casein from a cell involves extracting recombinant beta-casein from a concentrated suspension of cells using a water-miscible organic solvent. The water-miscible solvent contains from about 50% volume to about 95% volume of organic solvent and from about 50% to about 5% volume of water. The recombinant beta-casein is treated with a water-miscible organic solvent at a pH of from about 6.5 to about 8.5 and at a temperature of about 40° C. Examples of suitable organic solvents are acetone, isopropanol, ethanol or methanol.

After extraction of the recombinant beta-casein from the suspenion of cells, the recombinant beta-casein is isolated from the suspension of cells. After isolation, the recombinant beta-casein is concentrated to remove the water-miscible organic solvent. After concentration, the recombinant beta-casein is cooled to a temperature of about 5° C. to separate solids from the recombinant beta-casein. After cooling, the recombinant beta-casein is isolated from the solids.

After centrifugation, the recombinant beta-casein is treated wtih a water-soluble calcium salt. After treatment with the water-soluble calcium salt, the recombinant beta-casein is precipitated using an acid at a pH from about 3.5 to about 6.5. After precipitation, the recombinant protein is washed with a washing solution. Exemplary washing solutions are sodium acetate, citric acid, acetic acid, sodium citrate and the like. Finally, after washing, the recombinant protein is recovered.

DETAILED DESCRIPTION OF THE INVENTION

The present invention relates to a process for purifying and recovering a recombinant protein from a suspension of cells. As used herein the terms "purify", "purifying" or "purified" mean substantially free of other compounds. As will be apparent to those skilled in the art, any recombinant protein may be purified and recovered according to the process of the present invention. For example, recombinant proteins that can be purified and recovered pursuant to the process of the present invention include, but are not limited to, beta-casein.

The recombinant protein can be produced by any method known in the art. Typically, a gene that encodes the recombinant protein that is desired is inserted into a recombinant molecule. The polynucleotides constituting the gene may be obtained by standard procedures known in the art, such as from cloned DNA (such as a DNA "library"), chemical synthesis, cDNA cloning, or by the cloning of genomic DNA, or fragment thereof, from a desired cell as described in Sambrook, J., et al., *Molecular Cloning: A Laboratory Manual*, 2d Edition, Cold Spring Harbor Laboratory Press (1989).

Once the gene encoding the recombinant protein has been isolated, it is inserted into an appropriate cloning vector. A large number of vector-host systems known in the art may be used. Possible vectors include, but are not limited to, plasmids or modified viruses, provided that the vector system is compatible with the host cell used. The vectors that can be used include, for example, an *E. coli* cloning vector, bacteriophages such as lambda derivatives, plasmids such as pBR322 derivatives or pUC plasmid derivatives. The cloning vector can be introduced into host cells via transformation, transfection, infection, electroporation, etc., so that many copies of the gene sequence are generated.

Transformation of host cells with a cloning vector that incorporates the gene enables the generation of multiple copies of the gene. Therefore, the gene may be obtained in large quantities by growing transformants, isolating the cloning vector from the transformants and, when needed, retrieving the inserted gene from the isolated cloning vector.

Once sufficient copies of the gene sequence have been generated, the gene encoding the recombinant protein, or a functionally active fragment or other derivative thereof, can be inserted into an appropriate recombinant molecule. The recombinant molecule is a polynucleotide expression vector that contains the necessary elements for the transcription and translation of the inserted protein-coding sequence of the recombinant protein. Preferably, the expression vector also includes an origin of replication. The necessary transcription and translation signals can also be supplied by the native gene and/or its flanking regions.

Once a recombinant molecule has been prepared, it is inserted into an acceptable host cell which will grow and divide to produce clones. A variety of host cell-vector systems may be utilized to express the recombinant protein. Suitable host cell-vector systems include, for example, bacterial expression systems, mammalian cell systems infected with a virus, such as a vaccinia virus or adenovirus, insect cell systems infected with a virus such as a baculovirus, microorganisms such as yeast containing yeast vectors, and bacteria transformed with bacteriophage DNA, plasmid DNA or cosmid DNA.

Recombinant molecules containing the gene of interest can be identified by PCR amplification of the desired plasmid DNA or specific mRNA, nucleic acid hybridization, presence or absence of marker gene functions and expression of the inserted sequences. Once a suitable host system and growth conditions are established, the recombinant molecules containing the glycosyltransferase gene can be introduced into the host cells via any procedure known in the art such as transformation, transfection, infection, electroporation, etc.

The host cells, such as *E. coli* cells, transformed with a polynucleotide that encodes a recombinant protein of interest, can be added directly to a reaction vessel. If the host cells containing the gene express the recombinant protein into a culture medium, then the culture medium can be added directly to the reaction vessel.

To purify and recover the recombinant protein, the host cells are concentrated to form a concentrated suspension of whole cells. The host cells can be concentrated by any method known in the art. For example, the host cells may be centrifuged. Centrifugation removes water from the host cells and concentrates the cells, forming a cell paste. Centrifugation also separates the host cells from the culture medium where the recombinant protein is being expressed into a culture medium.

Once a concentrated suspension of cells has been obtained, the cells are placed in a reaction vessel and treated with a water-miscible organic solvent. Any water-miscible solvent can be used to extract the recombinant protein from the cell. The water-miscible solvent used in the extraction is preferably an aqueous solution containing from about 50% volume to about 95% volume of organic solvent and from about 50% volume to about 5% volume of water. Exemplary organic solvents that can be used in the process of the present invention include acetone, isopropanol, ethanol and methanol.

The extraction of the recombinant protein from the cells with the water-miscible solvent must take place at a pH of from about 5.0 to about 10.0 and at a temperature of from about 30° C. to about 50° C. Preferably, the pH is from about 6.5 to about 8.5 and the temperature is from about 35° C. to about 45° C. The molar ratio of cells to organic solvent in the reaction vessel is from about 1:1 to about 1:10, preferably from about 1:1 to about 1:5.

The water-miscible organic solvent extracts the recombinant protein from the suspension of cells. The water-miscible organic solvent is believed to selectively partition the recombinant protein from the suspension of cells and into a liquid phase. The liquid phase contains the recombinant protein, water-miscible solvent, water and low levels of proteinaceous impurities.

The extraction of the recombinant protein from the suspension of cells using the water-miscible organic solvent also purifies the recombinant protein. The purification results from the fact that the water-miscible solvent extracts mainly the recombinant protein from the suspension of cells while leaving a majority of the cellular debris and impurities behind.

After extraction of the recombinant protein from the suspension of cells, the liquid extract is isolated from the suspension of cells. The extract can be isolated from the cells using any technique known in the art. Preferably, the extract is isolated by centrifugation. When the extract is centrifuged, the extract is separated from the suspension of cells and is contained in the supernatant. The supernatant is then removed from the reaction vessel containing the suspension of cells and placed in a fresh reaction vessel.

After isolation of the liquid extract containing the recombinant protein from the cells, the extract is concentrated. The concentration removes most of the water-miscible organic solvent from the extract. The extract can be concentrated by any method known in the art. For example, if the extract is isolated from the suspension of cells by centrifugation, the supernatant containing the extract can be concentrated by reducing the pressure in the reaction vessel by using vacuum distillation. Vacuum distillation draws off liquid in the reaction vessel and concentrates the supernatant. The extract is concentrated to volume reductions from about 2 times to about 20 times, preferably from about 3 times to about 7 times. The target extract concentration is from about 30 to about 110 g/L, preferably from about 40 to about 70 g/L of total solids (recombinant protein and impurities) remaining in the extract.

After concentration, the concentrated liquid extract can be optionally cooled to a temperature of from about 0° C. to about 15° C., preferably to about 5° C. to about 10° C. When the extract is cooled, any solids or impurities present in the extract settle to the bottom of the reaction vessel. After cooling, the concentrated liquid extract is isolated from the solids and/or impurities using any method known in the art. For example, the extract can be isolated from the solids and/or impurities by centrifugation. Centrifugation separates the extract from any solids and/or impurities that have separated from the extract and settled to the bottom of the reaction vessel. The product is contained in the supernatant after centrifugation and can be removed from the reaction vessel using any procedure known in the art.

After removal of the solids and/or impurities, the concentrated extract containing the recombinant protein can optionally be treated with a water soluble calcium salt. Any water soluble calcium salt can be used in the process of the present invention. Examples of water-soluble calcium salts that can be used include calcium chloride, calcium acetate, calcium citrate and the like. The calcium salt can be added to improve the quality of the recombinant protein when it is later precipitated from the extract. The molar ratio of calcium salt to recombinant protein in the reaction vessel is from about 1:1 to about 1:10, preferably from about 1:2 to about 1:5.

After the addition of the water-soluble calcium salt, an acid can be optionally added to the concentrated extract if necessary in order to maintain the pH of the extract from about 3.5 to about 6.5. Any inorganic or organic acid can be used to adjust the pH of the extract. Examples of organic acids that can be used include carboxylic acids and dicarboxylic acids. Examples of carboxylic acids that can be used are acetic acid and formic acid. Examples of dicarboxylic acids that can be used include citric, oxalic, phthalic, sebacic and adipic acids. Examples of inorganic acids that can be used include phosphoric, hydrochloric, nitric and sulfuric acid.

Either after concentration or optionally, after calcium salt treatment, the concentrated extract containing the recombinant protein is acidified. When the concentrated extract is acidified, the recombinant protein is precipitated from the extract. The inorganic or organic acid identified above can also be used to precipitate the protein. The amount of acid to be used to precipitate the protein is determined by monitoring the pH. The precipitation of the recombinant protein from the concentrated extract must be conducted at a pH of from about 3.5 to about 6.5, preferably from about 5.0 to about 5.8. The precipitation of the recombinant protein using the acid further purifies the recombinant protein.

After precipitation, the precipitate containing the recombinant protein is filtered or centrifuged and then washed with a washing solution. The washing solution can be a solution of sodium acetate, acetic acid, citric acid, sodium citrate and the like. The washing of the precipitate with the washing solution is conducted at a pH of from about 3.5 to about 6.5, preferably from about 5.0 to about 5.8. At least one cake volume (10 to 25% of the original slurry volume) of washing solution is used. The precipitate is treated with a washing solution to remove any impurities that are entrapped within the precipitate. This washing of the precipitate with the washing solution results in the final purification of the recombinant protein.

If the recombinant protein purified pursuant to the process of the present invention is to be used for human consumption, the recombinant protein may optionally be treated after washing with a compound to improve or add to the flavor of the protein. For example, after washing with sodium acetate, the recombinant protein can be washed with citric acid, sodium citrate or the like to improve the flavor of the recombinant protein.

After washing of the recombinant protein with the washing solution, the recombinant protein is recovered. Once the recombinant protein is recovered, it may undergo further processing depending upon its intended use and/or final packaging requirements.

Proteins purified according to the present invention are from about 90 to about 97% pure, preferably about 92 to about 96% pure. The amount of recombinant protein recovered from the process of the present invention is from about 80 to about 90%.

As discussed earlier, the process of the present invention can be used to purify and recover any desired recombinant protein from a suspension of cells. In a preferred embodiment, the process of the present invention can be used to purify and recover recombinant beta-casein from host cells. Host cells producing recombinant beta-casein are centrifuged to form a suspension of cells (also referred to as a cell paste). The cell paste can be treated with an aqueous solution of 55% isopropanol at a pH of from about 6.5 to about 8.5 at a temperature of about 40° C. to extract the beta-casein from the cell paste and into the isopropanol and water ("liquid extract"). After extraction of the beta-casein from the cell paste, the liquid extract can be isolated from the cell paste by centrifugation. After centrifugation, the liquid extract can be concentrated by reducing the pressure. The extract can be concentrated to a concentration of from about 40 to about 70 g/L of total solids (recombinant protein and impurities) remaining in the extract. After concentration, the liquid extract can be cooled to 5 C. and then centrifuged. Any solids contained in the supernatant can be removed by processes known in the art.

After the removal of the solids, a water soluble calcium salt, can be added to the extract and the pH of the extract adjusted with an acid to precipitate the beta-casein. The precipitation of the beta-casein occurs at a pH of from about 5.0 to about 5.8. After precipitation of the beta-casein, the precipitate can be centrifuged and then washed with a solution of sodium acetate at a pH of about 5.4 to about 5.8. After washing with the sodium acetate, the beta-casein can be washed with citric acid. After washing with citric acid, the beta-casein can be recovered.

The following Examples illustrate the preferred embodiments of the process of the present invention and is not limiting of the specification and claims in any way.

EXAMPLE 1

100.0 g of cell biomass from a 40 L harvest were mixed with 500 mL of a 63% (v/v) isopropanol/water. The resultant slurry was adjusted to a pH of about 8.2 with dilute sodium hydroxide and held for about 1 hour at about 40° C. to facilitate complete extraction of the recombinant protein. The spent cells were removed by centrifugation, and the supernatant concentrated under reduced pressure to 42 g of total solids/L. The concentrate was cooled to about 5° C. to promote precipitation of impurities which were removed by centrifugation. Calcium chloride was added to the supernatant in a 1:1 molar ratio to the recombinant human beta-casein (determined by SDS-PAGE) and the solution adjusted to a pH of about 5.8 by the addition of sulfuric acid to initiate precipitation of protein. Product was recovered by filtration and washed with 2 cake volumes (100 mL) of 1% citric acid to yield 80 g of recombinant human beta-casein. Analysis by SDS-PAGE indicated protein purity of about 90 to about 95%.

EXAMPLE 2

100.0 g of cell biomass from a 500 L harvest were mixed with 500 mL of a 63% (v/v) isopropanol/water. The resultant slurry was adjusted to a pH of about 8.3 with dilute sodium hydroxide and held for about 1 hour at about 40° C. to facilitate complete extraction of the recombinant protein. The spent cells were removed by centrifugation, and the supernatant concentrated under reduced pressure to about 65 g of total solids/L. The concentrate was cooled to about 5° C. to promote precipitation of impurities which were removed by centrifugation. Calcium chloride was added to the supernatant in a 1:1 molar ratio to the recombinant human beta-casein (deterimined by SDS-PAGE) and the solution was divided into four equal aliquots. Each part was adjusted to a pH of about 5.8 by the addition of varying acids. Citric, hydrochloric, phosphoric, and sulfuric acid were used to initiate precipitation of the protein. The products were recovered by filtration and analyzed by SDS-PAGE to determine a protein purity of about 90 to about 95%.

EXAMPLE 3

22.0 g of cell biomass from a 750 L harvest were mixed with 88 mL of a 70% (v/v) isopropanol/water. The extract was recovered by centrifugation, and the remaining cells were extracted a second time with 88 mL of 60% (v/v) isopropanol/water. The spent cells were removed by centrifugation, and the two extracts were combined and concentrated under reduced pressure at about 40° C. The solution was adjusted to a pH of about 5.8 by the addition of dilute acetic acid to initiate precipitation of protein. Product was recovered by centrifugation, washed with 50 mM sodium acetate, and recentrifuged to recover the final product. Analysis by SDS-PAGE indicated protein purity of about 90 to about 95%.

EXAMPLE 4

37,000 L of whole cell culture were centrifuged. The recovered cell mass was suspended in distilled water and recentrifuged to a final volume of 4,900 L. The washed cells were extracted with a 73% (v/v) isopropanol/water solution (calculated using the cell volume). The pH of the slurry was adjusted to about 8.1 by addition of sodium hydroxide and maintained while the mixture was heated to about 40° C. and held for about 30 minutes. The spent cells were removed by centrifugation and the extract was filtered at ambient temperature. The resulting 8,090 L of filtrate was concentrated to a final volume of 3,370 L using a thin film evaporator and/or a pot still. The concentrated liquid extract was cooled to about 5° C. and the precipitated impurities were removed using a filter press. The beta-casein was precipitated by adding a molar equivalent of calcium chloride to the filtrate and lowering the pH to about 5.8 with hydrochloric acid. The product was isolated using a basket centrifuge. The beta-casein wet cake was washed with a citric acid solution and recentrifuged to yield 202.4 Kg of product. Analysis by SDS-PAGE indicated protein purity of about 90 to about 95%.

EXAMPLE 5

36,600 L of whole cell culture were centrifuged and the recovered cell mass was suspended in distilled water and recentrifuged to a final volume of 3,950 L. The washed cells were extracted with a 69% (v/v) isopropanol/water solution (calculated using the cell volume). The pH of the slurry was adjusted to about 8.1 by addition of sodium hydroxide and maintained while the mixture was heated to about 40° C. and held for about 30 minutes. The spent cells were removed by centrifugation, and the extract was filtered at ambient temperature. This resulted in 8,900 L of filtrate which was concentrated to a final volume of 2,680 L using a thin film evaporator and/or a pot still. The concentrated liquid extract was cooled to about 5° C., and the precipitated impurities were removed using a filter press. Calcium chloride was added to the filtrate in a 1:1 molar ratio to the beta-casein, and the pH was adjusted to about 5.8 with hydrochloric acid causing the beta-casein to precipitate out of solution. The product was isolated using a basket centrifuge. The beta-casein wet cake was then washed with a citric acid solution and recentrifuged to yield 135.7 Kg of product. Analysis by SDS-PAGE indicated protein purity of about 90 to about 95%.

What is claimed is:

1. A process of purifying and recovering recombinant beta-casein from a cell comprising the steps of:

extracting recombinant beta-casein from a concentrated suspension of cells using a water-miscible organic solvent selected from the group consisting of acetone, isopropanol, ethanol and methanol, said solvent containing from about 50% volume to about 95% volume organic solvent and from about 50% volume to about 5% volume water at a pH of from about 6.5 to about 8.5 and at a temperature of from about 30° C. to about 50° C., the molar ratio of suspension of cells to water miscible organic solvent being from about 1:1 to about 1:5;

isolating the recombinant beta-casein from the suspension of cells;

concentrating the recombinant beta-casein to remove the organic solvent;

cooling the recombinant beta-casein to a temperature of about 5° C. to separate solids from the recombinant beta-casein;

isolating the recombinant beta-casein from the solids;

treating the recombinant beta-casein with a water-soluble calcium salt, the molar ratio. of water-soluble calcium salt to recombinant beta-casein being from about 1:1 to 1:5;

precipitating the recombinant beta-casein using an acid;

washing the recombinant beta-casein with sodium acetate or acetic acid; and recovering the recombinant beta-casein.

2. The process of claim 1 wherein the suspension of cells is treated with an organic solvent at the temperature of about 40° C.

3. The process of claim 1 wherein the recombinant beta-casein is precipitated with the acid at a pH of from about 3.5 to about 6.5.

4. The process of claim 1 wherein the water-soluble calcium salt is selected from the group consisting of calcium chloride and calcium acetate.

5. The process of claim 1 further comprising the step of washing the recombinant beta-casein with citric acid after washing the recombinant beta casein with a compound selected from the group consisting of sodium acetate and acetic acid.

* * * * *